United States Patent
Parthasaradhi Reddy et al.

(10) Patent No.: US 7,705,142 B2
(45) Date of Patent: Apr. 27, 2010

(54) PROCESS FOR THE PREPARATION OF CEFIXIME

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Nagabelli Murali, Hyderabad (IN)

(73) Assignee: Hetero Drugs Limited, Hyderabad (IN)

( * ) Notice: Subject to any disclaimer, the term of this patent is extended or adjusted under 35 U.S.C. 154(b) by 92 days.

(21) Appl. No.: 10/598,877

(22) PCT Filed: Mar. 29, 2005

(86) PCT No.: PCT/IN2005/000094

§ 371 (c)(1),
(2), (4) Date: Sep. 14, 2006

(87) PCT Pub. No.: WO2006/103686

PCT Pub. Date: Oct. 5, 2006

(65) Prior Publication Data

US 2008/0242858 A1    Oct. 2, 2008

(51) Int. Cl.
*C07D 501/22*    (2006.01)
(52) U.S. Cl. .................................... 540/221
(58) Field of Classification Search .............. 540/221
See application file for complete search history.

(56) References Cited

U.S. PATENT DOCUMENTS

| 4,409,214 | A | 10/1983 | Takaya et al. | |
|---|---|---|---|---|
| 4,487,927 | A | 12/1984 | Takaya | |
| 6,313,289 | B1 | 11/2001 | Ludescher et al. | |
| 6,800,755 | B2 | 10/2004 | Deshpande et al. | |
| 6,825,345 | B2 * | 11/2004 | Decristoforo et al. | 540/222 |
| 6,894,162 | B2 * | 5/2005 | Kremminger | 540/222 |
| 7,355,041 | B2 * | 4/2008 | Greil et al. | 540/215 |
| 7,470,786 | B2 * | 12/2008 | Datta et al. | 544/227 |
| 2006/0252928 | A1 * | 11/2006 | Deshpande et al. | 540/222 |

FOREIGN PATENT DOCUMENTS

| AT | 405402 B | * | 6/1999 |
|---|---|---|---|
| EP | 30630 B1 | | 6/1981 |
| EP | 1721602 A1 | * | 11/2006 |
| GB | 2330140 A | | 4/1999 |
| GB | 2330141 A | | 4/1999 |
| WO | 95/33753 A1 | | 12/1995 |
| WO | 98/06723 A1 | | 2/1998 |
| WO | 98/31685 A1 | | 7/1998 |
| WO | 02/053563 A1 | | 7/2002 |

OTHER PUBLICATIONS

PCT, Notification of Transmittal of the Inernational Search Report and the Written Opinon of the Internatioal Searching Authority, PCT/1N/2005/000094.

Hideaky Yamanaka, et al., Synthesis and Biological Activity of a New Orally Active Cephalosporin, Cefixime (FK027), Central Research Laboratories, Fujisawa Pharmaceutical Co., Ltd. 2-1-6 Kashima, Yodogawa-ku, Osaka 532, Japan, *J Antibiot* (Tokyo), Dec. 1985;38(12)1738-51.

* cited by examiner

*Primary Examiner*—Mark L Berch
(74) *Attorney, Agent, or Firm*—Caesar, Rivise, Bernstein, Cohen & Pokotilow, Ltd.

(57) ABSTRACT

There is provided an improved process for preparing cefixime. Thus, for example, 7-amino-3-vinyl-3-cephem-4-carboxylic acid is reacted with 2-mercapto-1,3-benzothiazolyl-(Z)-2-(2-aminothiazol-4-yl)-2-(methoxycarbonyl)-methoxyimino acetate in tetrahydrofuran and water at 4° C. in the presence of triethylamine. The reaction mass is extracted with ethyl acetate. 7-[2-(2-Amino-4-thiazolyl)-2-(methoxycarbonylmethoxyimino)acetamido]-3-vinyl-3-cephem-4-carboxylic acid triethylamine salt present in the aqueous layer is hydrolyzed with sodium hydroxide in less than 30 minutes and aqueous hydrochloric acid is added immediately to adjust the pH to 4.8 to 5.2. Then, aqueous hydrochloric acid is added at 35° C. to adjust the pH 2.5 and cooled to crystallize cefixime trihydrate in high purity.

21 Claims, No Drawings

PROCESS FOR THE PREPARATION OF CEFIXIME

FIELD OF THE INVENTION

The present invention provides an improved process for the preparation of high purity cefixime.

BACKGROUND OF THE INVENTION

U.S. Pat. No. 4,409,214 disclosed 7-Acylamino-3-vinyl-cephalosporanic acid derivatives and pharmaceutically acceptable salts thereof. These compounds are antibacterial agents. Among them Cefixime, chemically 7-[2-(2-amino-4-thiazolyl)-2-(carboxymethoxyimino)acetamido]-3-vinyl-3-cephem-4-carboxylic acid is an orally active cephalosporin antibiotic and is more potent against gram-negative bacteria. Cefixime is represented by the following structure:

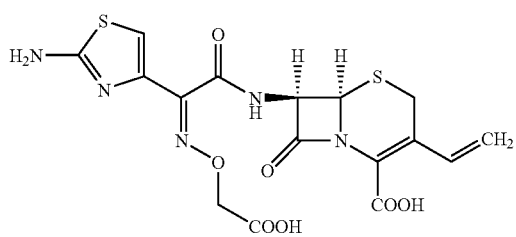

Processes for the preparations of Cefixime and related compounds were disclosed in U.S. Pat. No. 4,409,214, J. Antibiotics (1985), 38, 1738 and WO 95/33753, U.K. Patent Application No. 2 330 140, U.K. Patent Application No. 2 330 141, U.S. Pat. No. 6,313,289, WO 98/06723 and U.S. Pat. No. 6,800,755 B2.

U.K. Patent Application No. 2 330 141 described the process for preparing cefixime by hydrolyzing in a halogenated aliphatic hydrocarbon (e.g., methylenedichloride) ester compound of formula-A:

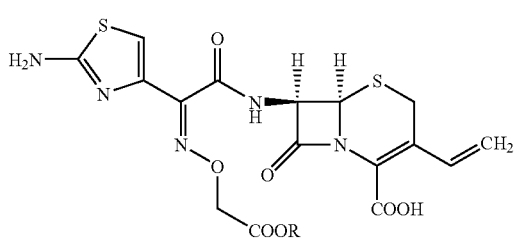

wherein R represents (C1-C4) alkyl group;

with potassium carbonate in the presence of phase transfer catalyst at ambient temperature for 30-90 minutes.

U.K. Patent Application No. 2 330 140 described a process for preparing cefixime by treating the compound of formula A with an inorganic base in dim ethyl formamide and water for 1 hour 30 minutes to 2 hours and isolating cefixime.

U.S. Pat. No. 6,800,755 B2 described a process for preparing cefixime by dissolving alkyl ester of formula A in water and water immiscible solvent such as ethyl acetate using sodium bicarbonate, hydrolyzing with sodium hydroxide at 0-25° C. and isolating cefixime by acidifying the reaction mass.

The processes described in U.K. Patent Application No. 2 330 141, U.K. Patent Application No. 2 330 140 and U.S. Pat. No. 6,800,755 B2 suffer from any of the following problems: a) color and quality are poor, b) contamination of cefixime with high boiling point solvent such as dimethyl formamide. The removal of the residual solvents is difficult owing to sensitivity of cefixime to high temperature.

J. Antibiotics (1985), 38, 1738 described processes for preparing cefixime involving protection and deprotection steps. The processes described required purification of cefixime by column chromatography. Methods involving column chromatographic purifications cannot be used for large-scale operations, thereby making the process commercially not viable.

Process for preparing cefixime described in U.S. Pat. No. 4,409,214 and WO 95/33753 are lengthy involving many protecting and deprotecting steps and so not commercially viable.

U.S. Pat. No. 6,313,289 B1 described the purification of cefixime by forming a crystalline amine salt of crude cefixime, converting the salt into sulfuric acid addition salt of cefixime and recovering pure cefixime from sulfuric acid addition salt of cefixime.

WO 98/06723 is related to cefixime dicyclohexyl amine salt and purification of cefixime via dicyclohexyl amine salt.

The purification of cefixime by the processes described in U.S. Pat. No. 6,313,289 B1 and WO 98/06723 are lengthy and complicated involving many crystallizations, neutralizations and salt formations.

The present invention is an improved, commercially viable process solving the aforesaid problems associated with processes described in the prior art.

SUMMARY OF THE INVENTION

According to the present invention, there is provided an improved process for preparing cefixime of formula I:

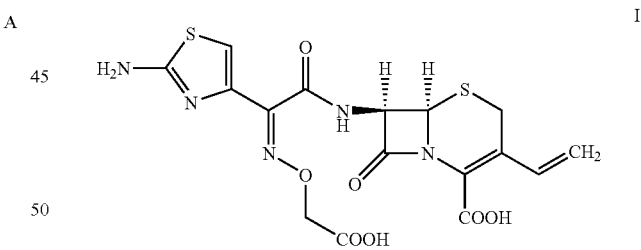

which comprises:

a) reacting 7-amino-3-vinyl-3-cephem-4-carboxylic acid of formula III:

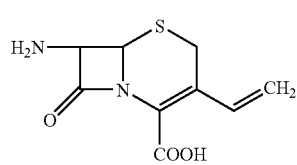

with a thiazolyl acetic acid derivative of formula IV:

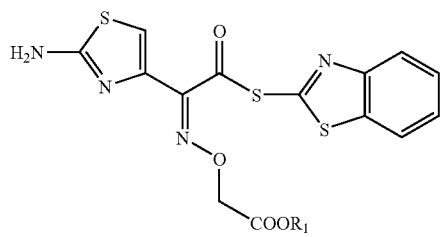

wherein $R_1$ represents lower alkyl in a mixture of water and non-protic water miscible solvent in the presence of a base of formula V:

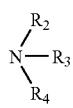

wherein $R_2$, $R_3$ and $R_4$ independently of each other represents hydrogen, alkyl, cycloalkyl, alkylaryl, aryl or aralkyl, to obtain a reaction mass comprising a salt of compound of formula II:

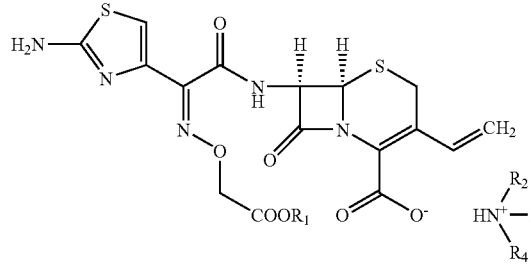

wherein $R_1$, $R_2$, $R_3$ and $R_4$ are same as defined above;
b) extracting the reaction mass of step (a) with ethyl acetate or methylene dichloride and separating the aqueous layer;
c) hydrolyzing the salt of formula II present in the separated aqueous layer using an aqueous alkali metal hydroxide solution at about 0–15° C.;
d) adding an acid immediately after completion of hydrolysis reaction to adjust the pH to about 4.5 to 8.0; and
e) crystallizing cefixime of formula I by adjusting the pH of the resulting solution of step (d) to about 2.0 to 3.5 with an acid and cooling if required.

DETAILED DESCRIPTION OF THE INVENTION

According to the present invention, there is provided a process for preparing cefixime of formula I:

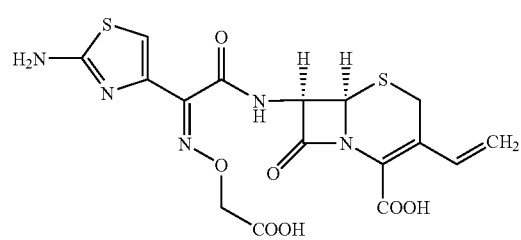

According to the present invention, 7-amino-3-vinyl-3-cephem-4-carboxylic acid of formula III:

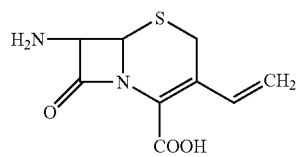

is reacted with a thiazolyl acetic acid derivative of formula IV:

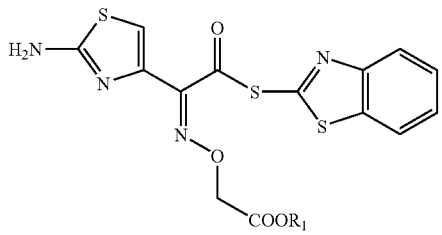

wherein $R_1$ represents lower alkyl in a mixture of water and non-protic water miscible solvent in the presence of a base of formula V:

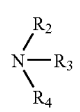

wherein $R_2$, $R_3$ and $R_4$ independently of each other represents hydrogen, alkyl, cycloalkyl, alkylaryl, aryl or aralkyl to obtain a reaction mass comprising the compound of formula II:

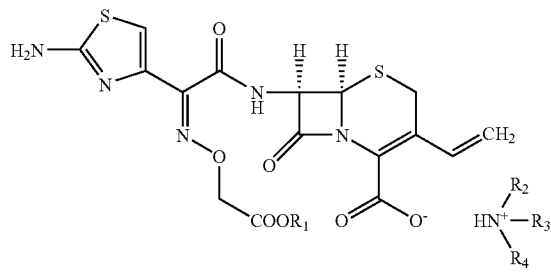

II wherein $R_1$, $R_2$, $R_3$ and $R_4$ are as defined above.

Preferably the reaction is carried out at below about 15° C., more preferably at about 0-10° C.

Preferably non-protic water miscible solvent is selected from tetrahydrofuran, acetone, dimethylsulfoxide and a mixture thereof. The more preferable solvent used is tetrahydrofuran.

Preferably at least about 1 mole of compound of formula IV per mole of compound of formula III may be used and more preferably 1.0 to 1.5 moles of compound of formula IV per mole of compound of formula III may be used.

The preferable bases are the compounds of formula V wherein $R_2$, $R_3$ and $R_4$ independently of each other represents hydrogen, alkyl or cycloalkyl. More preferable bases are amine bases such as triethylamine, trimethylamine, tributylamine and n-butylamine.

The quantity of the base of formula V used is at least about 1 mole per mole of compound of formula III, preferably about 1 to 2 moles per mole of compound of formula III and more preferably about 1 to 1.4 moles per mole of the compound of formula III is used.

The ratio of non-protic water miscible solvent to water is not critical but preferably the ratio is about 5.0 to 0.2.

The reaction mass obtained above is extracted with ethyl acetate or methylenedichloride solvent. The more preferable solvent is ethyl acetate.

The extraction step removes non-protic water miscible solvent from the reaction mass along with water immiscible impurities, leaving the salt of formula II in the aqueous medium.

The reaction mass obtained after the extraction may preferably be filtered to remove any insoluble matter.

According to known processes, the amine salts formed are neutralized and then free ester of formula II thus formed is precipitated as a method of purification of the ester compound; or the amine salts are isolated as crystalline solids as a method of purification. The salts thus separated has to be further processed, adding additional steps, to get finally cefixime.

The present invention ensures that high purity cefixime can be obtained without a need for isolation of the salts of formula II or the corresponding free compound so as to obtain pure cefixime.

The present invention also achieves the objective of avoiding neutralization step of the salt of formula II to obtain the compound in free form; and crystallization and dissolution of the free form thus formed to proceed further to obtain cefixime.

After extraction step, the salt of formula II present as aqueous solution is subjected to ester hydrolysis with an aqueous alkali metal hydroxide solution at about 0-15° C. Preferably the reaction is carried out at about 0-10° C.

Alkali metal hydroxide used is preferably sodium hydroxide or potassium hydroxide.

The quantity of alkali metal hydroxide used is at least about 2 moles per mole of the compound of formula III, preferably about 2.5 to 4.0 moles per mole of the compound of formula III and more preferably about 2.8 to 3.5 moles per mole of the compound of formula III.

It takes longer time for hydrolysis in the presence of organic solvents. Thus for example, it takes at least about 1 hour 30 minutes in aqueous medium in the presence of dimethyl formamide.

There is an adverse effect of development of color to the cefixime formed and formation of undesirable impurities in the cefixime obtained when the hydrolysis is carried out for longer duration.

We have found that hydrolysis step is completed in less than about 30 minutes under the condition of the present invention.

Immediately after the completion of the hydrolysis, the pH of the reaction mass is adjusted to about 4.5 to 8.0, preferably about 4.5 to 6.0 using an acid.

Preferably the acid used is aqueous hydrochloric acid, aqueous sulfuric acid or aqueous phosphoric acid.

After the neutralization step, cefixime is crystallized from the aqueous solution by adjusting the pH to about 2.0 to 3.5 with an acid and cooling is required to affect the crystallization. The contents may optionally be seeded to initiate crystallization.

Typically, cefixime crystallized is as cefixime trihydrate of formula Ia:

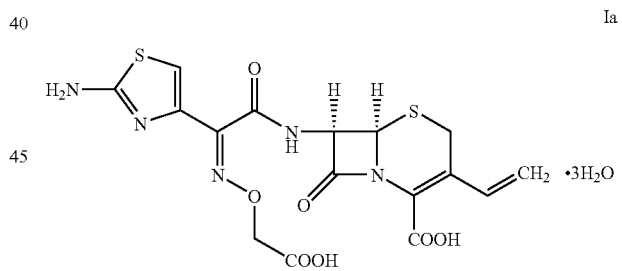

Ia

Preferable acids used are aqueous hydrochloric acid or aqueous sulfuric acid.

If not otherwise defined herein alkyl includes ($C_1$-$C_{10}$)-alkyl; lower alkyl includes ($C_1$-$C_4$)-alkyl; cycloalkyl includes ($C_3$-$C_8$)-cycloalkyl, preferably ($C_5$-$C_6$)-cycloalkyl; and aryl includes ($C_6$-$C_{12}$)-aryl, preferably phenyl.

A still preferred process of invention is described as below: 7-amino-3-vinyl-3-cephem-4-carboxylic acid of formula III is reacted with a thiazolyl acetic acid derivative of formula IV wherein $R_1$ is methyl or ethyl in a mixture of water and tetrahydrofuran in the presence of triethylamine, trimethylamine or tributylamine in at least about 1 mole per mole of compound of formula III used, more preferably about 1 to 1.4 moles per mole of compound of formula III used to obtain a reaction mass comprising the compound of formula II

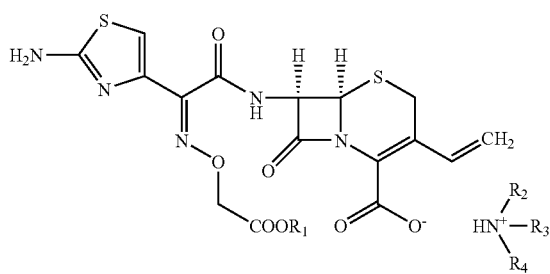

wherein $NR_2R_3R_4$ represents $Et_3N$, $Me_3N$ or $(butyl)_3N$ and $R_1$ represent methyl or ethyl.

The reaction mass is extracted with ethyl acetate or methylene chloride, preferably with ethyl acetate. After extraction, aqueous layer is separated.

Aqueous alkali metal hydroxide solution, preferably aqueous NaOH solution containing about 2.5 to 4.0 moles of the alkali metal hydroxide per mole of the compound of formula III used is added at once to the separated aqueous layer, stirring for less than about 30 minutes, preferably about 5-20 minutes, at about 0-10° C. Aqueous hydrochloric acid is added to the resulting reaction mass immediately so as to adjust the pH to about 4.5-8.0, preferably to about 4.5 to 6.0. Then, aqueous acid such as aqueous hydrochloric acid is added to adjust the pH of solution to about 2.0-3.5, cooled if necessary, to crystallize cefixime as cefixime trihydrate.

The compounds of formulae III and IV are known and can be obtained from known methods.

The invention will now be further described by the following example, which is illustrative rather than limiting.

REFERENCE EXAMPLE

A) Sodium acetate (120 gm) is added to water (400 ml) and thiourea (41.6 gm) at 25-30° C., cooled to 12° C. and then (Z)-4-chloro-2-[[(methoxycarbonyl)methoxy]imino]acetoacetic acid (100 gm) Is added at 12° C. The contents are stirred for 3 hours at 25-30° C., cooled to 5° C., pH is adjusted to 3.0 with conc. hydrochloric acid at 5-0° C. Then the reaction mass is cooled to 0° C. and stirred for 1 hour at 0-5° C. The resulting solid is filtered, washed two times with chilled water (each time 100 ml) and dried at 100-105° C. to give 95 gm of (Z)-2-(2-aminothiazol-4-yl)-(methoxycarbonyl)methoxyimino acetic acid (High Performance Liquid Chromatographic (HPLC) purity: 99.5%).

B) 2,2'-Dithiobis(benzothiazole) (117.75 gm) and acetonitrile (580 ml) are added to (Z)-2-(2-aminothiazol-4-yl)-(methoxycarbonyl)methoxyimino acetic acid (75 gm) at 25-30° C. and then distilled off 50 ml of acetonitrile under vacuum at 45-50° C. The contents are cooled to 25° C. under $N_2$ atmosphere, flushed with 20 ml of acetonitrile and cooled to 13° C. Triethylamine (30 gm) is added to the contents at 13° C., stirred for 30 minutes at 13° C. under $N_2$ atmosphere and then cooled to 0° C. Triphenylphosphine (96 gm) is added to the reaction mass at 0° C., stirred for 1 hour at 0-2° C. and cooled to −10° C. Then the reaction mass is stirred for 4 to 5 hours at −10° C., filtered the mass and washed with chilled methanol. Methanol (470 ml) is added to the reaction mass at 25° C., cooled to −5° C. under $N_2$ atmosphere, the wet cake is added for 5 minutes at −5° C. and stirred for 1 hour at −5° C. Filtered the mass, washed with methanol (100 ml) and dried to yield 93.75 gm of 2-mercapto-1,3-benzothiazolyl-(Z)-2-(2-aminothiazol-4-yl)-2-(methoxycarbonyl)-methoxyimino acetate (HPLC purity 98.2%).

EXAMPLE

Tetrahydrofuran (340 ml) is added to water (350 ml) and cooled to 4° C., 7-amino-3-vinyl-3-cephem-4-carboxylic acid (25 gm) and 2-mercapto-1,3-benzothiazolyl-(Z)-2-(2-aminothiazol-4-yl)-2-(methoxycarbonyl)-methoxyimino acetate (55 gm) are added at 4° C. Then the mixture of triethylamine (12 gm) and tetrahydrofuran (350 ml) is slowly added for 2 hours at 4° C., stirred for 4 hours at the same temperature. Then ethyl acetate (250 ml) is added. The contents are filtered through high-flow bed and washed the bed with ethyl acetate (100 ml). The aqueous layer is separated and washed with ethyl acetate (350 ml) at 14° C. The combined organic layer is extracted with water (110 ml). Eno carbon (2.5 gm) is added to the combined aqueous layer containing 7-[2-(2-amino-4-thiazolyl)-2-(methoxycarbonyl-methoxyimino)acetamido]-3-vinyl-3-cephem-4-carboxylic acid triethylamine salt at 25° C., stirred for 30 minutes, filtered through high-flow bed and washed the bed with water (300 ml). The filtrate is cooled to 0° C., sodium hydroxide solution (13.5 gm NaOH in 75 ml of water) is added at once and stirred for 15 minutes at 0-8° C. Then 30 ml of 1:1 hydrochloric acid is added to the reaction mass at once to adjust the pH to 4.8-5.2. Eno carbon (5 gm) is added to the reaction mass at 15-20° C., stirred for 15 minutes, filtered and washed with water (166 ml). Then ethylenediaminetetraacetic acid, disodium salt (EDTA, 0.25 gm) is added to the above filtrate at 20-25° C., temperature is raised to 35° C. and pH is adjusted to 2.5 with 1:1 Hydrochloric add. The reaction mass is seeded with cefixime trihydrate, stirred for 30 minutes at 35° C. and cooled to 30° C. Then the reaction mass is stirred for 3 hours at 30-32° C., again cooled to 2° C. and stirred for 1 hour at 2-5° C. The resulting solid is filtered, washed three times with chilled water (each time 110 ml) and dried to give 40 gm of white crystalline cefixime trihydrate (water content 11.1%, HPLC purity: 99.9%, tetrahydrofuran by Gas Chromatography (GC): not detected, ethyl acetate by GC: not detected).

What is claimed is:

1. A process for preparing cefixime of formula I:

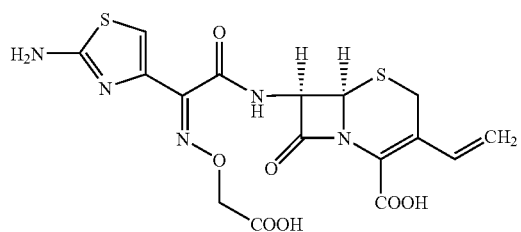

which comprises,
a) reacting 7-amino-3-vinyl-3-cephem-4-carboxylic acid of formula III:

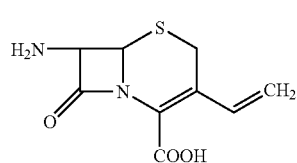

with a thiazolyl acetic acid derivative of formula IV:

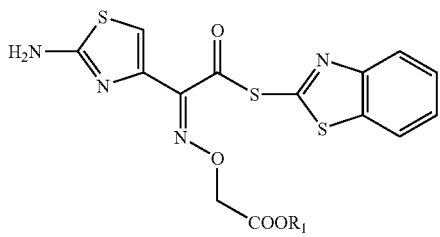

wherein R1 represents lower alkyl in a mixture of water and non-protic water miscible solvent in the presence of a base of formula V:

wherein R2, R3 and R4 independently of each other represents hydrogen, alkyl, cycloalkyl, alkylaryl, aryl or aralkyl to obtain a reaction mass comprising the compound of formula II:

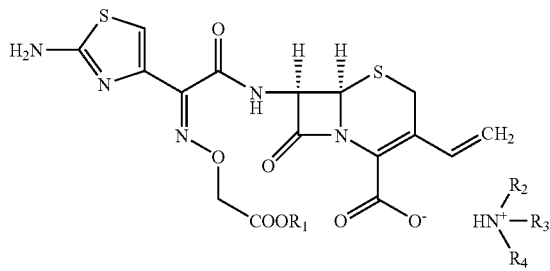

wherein R1, R2, R3 and R4 are as defined above;
   b) extracting the reaction mass of step (a) with ethyl acetate or methylene dichloride and separating the aqueous layer;
   c) hydrolyzing the salt of formula II present in the separated aqueous layer using an aqueous alkali metal hydroxide solution at about 0-15° C.;
   d) adding an acid immediately after completion of hydrolysis reaction to adjust the pH to about 4.5 to 8.0; and
   e) crystallizing cefixime of formula I by adjusting the pH of the resulting solution of step (d) to about 2.0 to 3.5 with an acid and cooling if required.

2. The process according to claim 1, wherein the reaction in step (a) is carried out at below about 15° C.

3. The process according to claim 2, wherein the reaction in step (a) is carried out at about 0-10° C.

4. The process according to claim 1, wherein the non-protic water miscible solvent is selected from tetrahydrofuran, acetone, dimethylsulfoxide and a mixture thereof.

5. The process according to claim 4, wherein the non-protic water miscible solvent is tetrahydrofuran.

6. The process according to claim 1, wherein R2, R3 and R4 of formula V independently of each other represent hydrogen, alkyl or cycloalkyl.

7. The process according to claim 1, wherein the base is selected from triethylamine, trimethylamine, tributylamine and n-butylamine.

8. The process according to claim 1, wherein the quantity of the base of formula V used is at least about 1 mole per mole of compound of formula III.

9. The process according to claim 8, wherein the quantity of the base of formula V used is about 1 to 1.4 moles per mole of compound of formula III.

10. The process according to claim 1, wherein the solvent used in step (b) is ethyl acetate.

11. The process according to claim 1, wherein the hydrolysis reaction in step (c) is carried out at about 0-10° C.

12. The process according to claim 1, wherein the alkali metal hydroxide is sodium hydroxide or potassium hydroxide.

13. The process according to claim 1, wherein the quantity of alkali metal hydroxide is at least about 2 moles per mole of the compound of formula III.

14. The process according to claim 13, wherein the quantity of alkali metal hydroxide is about 2.5 to 4.0 moles per mole of the compound of formula III.

15. The process according to claim 14, wherein the quantity of alkali metal hydroxide is about 2.8 to 3.5 moles per mole of the compound of formula III.

16. The process according to claim 1, wherein the pH of the reaction mass in step (d) is adjusted to about 4.5 to 6.0 with an acid.

17. The process according to claim 1, wherein the acid used in step (d) is selected from aqueous hydrochloric acid, aqueous sulfuric acid and aqueous phosphoric acid.

18. The process according to claim 17, wherein the acid in step (d) is aqueous hydrochloric acid.

19. The process according to claim 1, wherein the acid in step (e) is selected from aqueous hydrochloric acid and aqueous sulfuric acid.

20. The process according to claim 19, wherein the acid in step (e) is aqueous hydrochloric acid.

21. The process according to claim 1, wherein the cefixime which is crystallized in step (e) is a cefixime trihydrate of formula Ia:

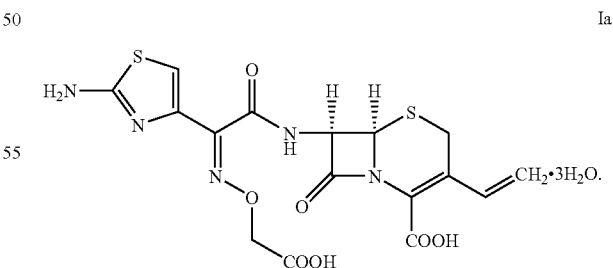

* * * * *